United States Patent [19]

Samat et al.

[11] 4,052,218
[45] Oct. 4, 1977

[54] NOVEL SPIRO-HETEROCYCLIC COMPOUNDS, THEIR PREPARATION, AND USE THEREOF IN A THERMOGRAPHIC RECORDING MATERIAL

[75] Inventors: André Samat; Robert Guglielmetti, both of Brest; Jacques Metzger, Marseille, all of France

[73] Assignee: Laboratoires de Physicochimie Appliquee I S S E C, Ferney Voltaire, France

[21] Appl. No.: 579,119

[22] Filed: May 19, 1975

[30] Foreign Application Priority Data

May 24, 1974 France ................ 74.18078

[51] Int. Cl.² .............................. G03C 1/02
[52] U.S. Cl. .................... 96/114.1; 96/90 PC; 250/316; 260/304 R; 346/135; 542/401
[58] Field of Search ............. 260/304, 240.7, 90 PC; 96/114.1

[56] References Cited

U.S. PATENT DOCUMENTS

| 3,299,079 | 1/1967 | Taylor ............................ 260/240 G |
| 3,320,061 | 5/1967 | Taylor ............................ 96/90 PC |
| 3,871,886 | 3/1975 | Robillard ....................... 96/90 PC |
| 3,896,126 | 7/1975 | Oberlinner et al. .......... 260/240 D |
| 3,923,524 | 12/1975 | Haase ............................ 96/90 PC |

FOREIGN PATENT DOCUMENTS

| 406,257 | 1/1966 | Switzerland |
| 444,197 | 9/1967 | Switzerland |

OTHER PUBLICATIONS

Gautron Chem. Abstracts 66 (1967) No. 105903.
Tolmachev et al., Ukr. Khim, Zh, 1971 37 (9) pp. 927-934.

*Primary Examiner*—Arthur P. Demers
*Attorney, Agent, or Firm*—Lowe, King, Price & Markva

[57] ABSTRACT

The invention relates to novel thermochromic spiro heterocyclic compounds having one or the other of the following formulae:

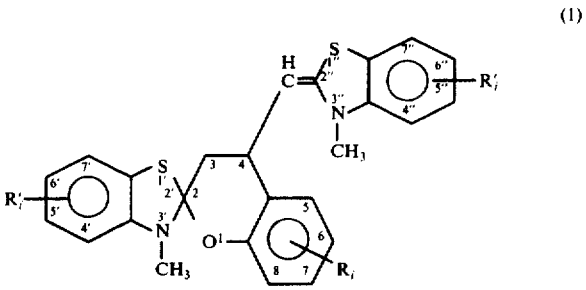

(1)

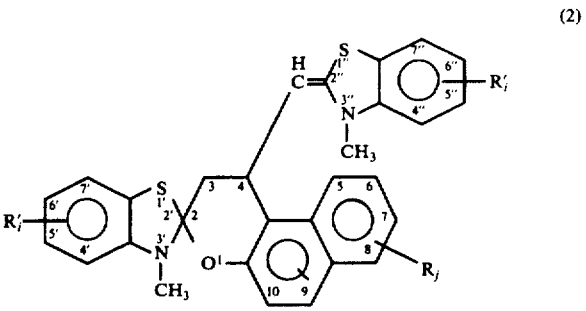

(2)

where $R_1$ denotes hydrogen atoms or one or more electron-donor groups in positions 5, 6, 7 and 8 in formula (1); $R_i'$ denotes hydrogen atoms or one or more electron-donor or electron-acceptor groups in positions 4', 5', 6' and 7' and 4'', 5'', 6'' and 7'' in formulae (1) and (2); and $R_j$ denotes hydrogen atoms or one or more electron-donor groups in positions 5, 6, 7, 8, 9 and 10 in formula (2). Use in thermographic recording material.

7 Claims, No Drawings

NOVEL SPIRO-HETEROCYCLIC COMPOUNDS, THEIR PREPARATION, AND USE THEREOF IN A THERMOGRAPHIC RECORDING MATERIAL

The invention relates to novel spiro-heterocyclic compounds having one or the other of the following general formulae:

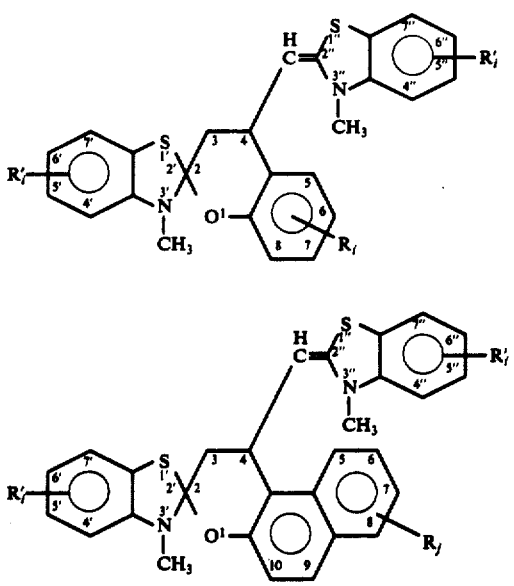

wherein $R_i$ denotes hydrogen atoms or one or more electron-donor groups in positions 5, 6, 7 and 8 in formula (1);

$R_i'$ denotes hydrogen atoms or one or more electron-donor or electron-acceptor groups in positions 4', 5', 6' and 7' and 4", 5", 6" and 7" in formulae (1) and (2); and $R_j$ denotes hydrogen atoms or one or more electron-donor groups in positions 5, 6, 7, 8 9 and 10 in formula (2).

The following are non-limitative examples of electron-donor groups: alkyl radicals and the groups OH, OR, $NH_2$, $NR_1R_2$ and NHCOR, where R, $R_1$ and $R_2$ each denote an alkyl radical.

The following are non-limitative examples of electron-acceptor groups: the groups $NO_2$, C≡N, $HSO_3$,

COR, COOH, and COOR where R denotes an alkyl radical, and halogen atoms.

The invention also relates to a method of preparing the compounds according to the invention, wherein a quaternary benzothiazolium salt having the formula:

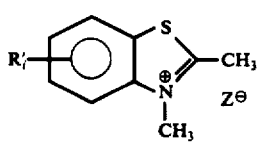

where $R_i'$ is as defined hereinbefore and Z is an anion, e.g. a paratoluene sulphonate or iodide group, is condensed with a hydroxy-2-benzoic or orthohydroxy-naphthoic aldehyde, which may or may not bear the substituent groups $R_i$ and $R_j$ respectively.

The condensation reaction is performed in the presence of a base, e.g. piperidine, in a suitable solvent such as ethanol or acetone.

The quaternary salt having the formula (3) can be obtained by well-known methods such as cyclisation in the presence of acetic anhydride of an ortho-aminothiophenol, which may or may not be substituted, or of its zinc salt, the resulting base being converted into the desired quaternary salt e.g. by reaction with methyl p-toluene sulphonate.

The novel compounds according to the invention are thermochromic compounds which change colour when heated to a temperature above their colour-change temperature, which is usually of the order of 180° C or above, depending on the particular compound.

The invention also relates to the use of the novel compounds according to the invention in a thermographic recording material, and the material thus obtained.

Usually the thermographic recording material comprises a suitable substrate, e.g. a sheet of paper, a film of synthetic polymer or a thin metal sheet, coated with a layer of thermochromic composition comprising at least one compound according to the invention and a suitable binder. Frequently, the thermosensitive composition also comprises a reagent capable of reacting with the compound according to the invention to give a distinctive colour when whichever of the reagent and the compound which has the lower melting-point is heated above the melting-point thereof. Then, the reagent or the compound becomes liquid and reacts by contact with the other substance, producing a colour.

When the compound according to the invention is used alone with a binder, the compound may be in the form of a solution, emulsion or fine dispersion. When the compound according to the invention is used in association with a reagent and a binder, the compound and the reagent should be in the form of fine solid particles which are uniformly dispersed or emulsified in the binder or a binder solution, to prevent the compound and reagent from reacting prematurely, as they would do if they were in solution.

The reagents used may e.g. be phenol compounds melting above approx. 60° C, metal salts wherein the metal ion can be chelated with the compounds according to the invention, sequestering agents, etc..

Swiss Specifications Nos. 406,257 and 444,197 and French Specification No. 72 37857 contain lists of phenol compounds and metal salts adapted for use in association with the compounds according to the invention. The aforementioned specifications and applications also contain details about the binders and the formulation of thermographic compositions for use according to the invention.

The following are examples of preferred reagents for use in the recording materials according to the invention:

1. bis-2,2-(para-hydroxyphenyl)propane
2. zinc stearate
3. cobalt stearate
4. manganese stearate
5. copper stearate
6. zinc chloride
7. manganese chloride It is often advantageous to use a reagent in association with a compound according to the invention, since the resulting colour change is clearer than when the composition according to the invention is used alone. The reagent can also lower the colour-change temperature below that of the compound according to the invention by itself, since the reagent often has a lower melting-point than the compound according to the invention. Again, a reagent can be used to obtain different colours from those given by the compound according to the invention by itself. The reagent, if used, is preferably present in or approximately in the stoichiometric proportion.

Use may be made of practically any binder of known use in photographic emulsions, thermographic compositions and similar arts. For example, polyvinyl alcohol, methyl cellulose, hydroxyethyl cellulose, or various polymers may be used. Polyvinyl alcohol is the preferred binder. The following non-limitative examples are given to illustrate the preparation and use of the compounds according to the invention.

EXAMPLE 1:

Synthesis of a compound having the formula:

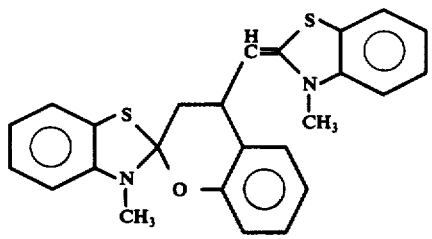

125 g of orthoaminothiophenol in 125 cm³ chloroform were dissolved in a 500 cc 3-necked flask provided with an agitator, a reflux condenser and a dropping funnel. 3 g of powdered zinc were added and the solution was refluxed, after which the heating was switched off. 102 g of acetic anhydride were added dropwise, after which the chloroform reflux was automatically maintained by the reaction.

At the end of the addition process, the mixture was refluxed for 30 minutes, and was then left to cool and filtered. The filtrate was washed twice in water and then in sodium carbonate solution, and then decanted. The chloroform was evaporated, followed by distillation at reduced pressure. The base (2-methyl benzothiazole) was recovered.

B.P. (20 mm Hg) = 123°-4° C - Yield: 78%.

22.4 g of the base and 28 g methyl tosylate were placed in a 100 c.c. flask provided with a condenser comprising a $CaCl_2$ trap, and heated to 120° C in an oil bath for two hours. The quaternary salt formed with anhydrous acetone was recovered and recrystallised from ethanol.

M.P. = 186° C - Yield: 95%.

10.05 g of quaternary salt (3 × $10^{-2}$ mol) and 1.9 g (slightly more than 1.5 × $10^{-2}$ mol) of salicylaldehyde in 400 cm³ absolute ethanol were placed in an Erlenmeyer flask provided with a magnetic agitator and surrounded with aluminium paper. 3 cm³ (3 × $10^{-2}$ mol) of piperidine were added, followed by agitation at room temperature for one hour. The mixture was filtered and the precipitate was washed in alcohol. 3.8 g of a blue-green product was obtained (yield: 59%).

M.P. = 165°-170° C.

EXAMPLE 2:

Synthesis of the compound having the formula:

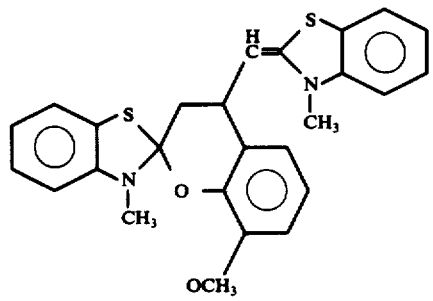

The quaternary salt of benzothiazolium was obtained as described in the first two steps of Example 1.

10.05 g (3 × $10^{-2}$ mol) of quaternary salt and 2.5 g (slightly more than 1.5 × $10^{-2}$ mol) orthovanillin were placed in an Erlenmeyer flask surrounded with aluminium-paper and provided with a dropping funnel and magnetic agitation. 3 cm³ of piperidine dissolved in 40 cm³ acetone were added dropwise during 20 minutes, agitation being maintained at room temperature. After the addition, agitation was continued for 5 minutes, followed by filtering.

The precipitate was washed in ethanol and then in acetone. 5.1 g of a white product were obtained (yield = 74%).

M.P. = 170°-175° C.

EXAMPLE 3:

Synthesis of the compound having the formula:

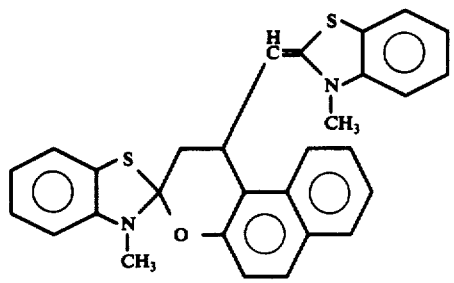

The quaternary salt of benzothiazolium was obtained as described in the first two steps of Example 1.

10.05 g (3 × $10^{-2}$ mol) of quaternary salt and 2.7 g 2-hydroxy-α-naphthaldehyde (slightly more than 1.5 × $10^{-2}$ mol) in 150 cm³ acetone were placed in an Erlenmeyer flask surrounded with aluminium paper and equipped with a magnetic agitator. 3 cm³ of piperidine dissolved in 30 cm³ acetone were slowly added, agitation being maintained at room temperature. After the addition, agitation was continued for 4 hours, followed by filtering.

The precipitate was washed in water, ethanol and then in acetone. 4.5 g of a pale-blue product were obtained (yield = 62° C). M.P. = 172°-176° C.

The compounds in Examples 1–3 are characterised by the following nuclear magnetic resonance spectra (solvent $CDCL_3$):

| Compound in Example | NATURE OF SIGNAL, δ in ppm/TMS, integration | | | | | |
|---|---|---|---|---|---|---|
| 1 | multiplet 2.5 to 2.85 2H | singulet 3.07 3H | singulet 3.16 3H | multiplet 3.6 to 4.2 1H | doublet 4.45 1H | multiplet 6.5 to 7.5 12H |
| 2 | multiplet 2.35 to 2.70 2H | singulet 3.05 3H | singulet 3.08 3H | singulet 3.64 3H | multiplet 3.50 to 3.90 1H | doublet 4.35 1H multiplet 6.40 to 7.10 11H |
| 3 | multiplet 2.80 to 3.20 2H | singulet 3.08 3H | singulet 3.13 3H | multiplet 3.50 to 4.50 1H | doublet 4.88 1H multiplet 6.40 to 7.2 14H | |

EXAMPLE 4

This Example illustrates the use of the compounds according to the invention in thermographic recording elements.

The following thermochromic compositions were prepared:

| | |
|---|---|
| Composition A | |
| Compound of Example 1 | 0.02 g |
| 10% solution of polyvinyl alcohol in water (binder) | 1 g |
| Composition B | |
| Compound of Example 1 | 0.02 g |
| Bis-2,2-(p-hydroxyphenyl)propane (reagent) | 0.05 g |
| 10% solution of polyvinyl alcohol in water (binder) | 1 g |
| Composition C | |
| Compound of Example 1 | 0.02 g |
| Zinc stearate (reagent) | 0.02 g |
| 10% solution of polyvinyl alcohol in water (binder) | 1 g |
| Composition D | |
| Compound of Example 3 | 0.01 g |
| Compound of Example 1 | 0.01 g |
| 10% solution of polyvinyl alcohol in water (binder) | 1 g |

Compositions A to D are prepared by preparing suitably homogenised emulsions of finely-divided particles of one or more thermosensitive compounds according to the invention and of the reagent, if required, in the binder solution.

Next, thermographic recording elements are prepared by applying each composition in the form of a thin layer (e.g. having a thickness of the order of 10–50 microns) by any suitable method, e.g. by a doctor, to a paper or other substrate, after which the applied layer is dried e.g. in hot air.

If the applied composition consists of particles of thermosensitive compound and binder only, a colour trace appears when the element bearing the composition is subjected to a temperature above the colour-change temperature of the compound, e.g. by means of a heated-tip probe forming part of a recording device.

If the applied composition consists of a mixture of particles of thermosensitive compound and of a reagent and binder, when the element bearing the composition is subjected to a temperature above the melting-point of the compound or of the reagent having the lower melting-point, one of the two constituents melts and reacts by contact with the other, producing a colour. As before, heating can be applied by a heated-point probe forming part of a recording device, in which case the colour trace is obtained.

The final colour obtained depends on the particular composition used.

The following Table shows some examples of the colour obtained with the compounds in Examples 1-3, used either without a reagent or with the aforementioned reagents (1)-(7).

TABLE

| BINDER: 10% POLYVINYL ALCOHOL IN WATER | | | |
|---|---|---|---|
| COMPOUND IN EXAMPLE | RE- AGENT | INITIAL COLOUR | COLOUR OBTAINED BY HEATING |
| 1 | without | pale-yellow | reddish brown |
| | (1) | colourless | red |
| | (2) | pale yellow | reddish brown |
| | (3) | pale yellow | reddish brown |
| | (4) | pale yellow | reddish brown |
| | (5) | pale yellow-green | reddish brown |
| | (6) | colourless | orange-red |
| | (7) | colourless | orange-red |
| 2 | without | pale yellow | blue |
| | (1) | colourless | brownish-violet |
| | (2) | pale yellow-grey | reddish-brown |
| | (3) | pale yellow-grey | brownish-violet |
| | (4) | pale yellow-grey | brownish-violet |
| | (5) | pale yellow-green | brown |
| | (6) | colourless | red |
| | (7) | colourless | reddish brown |
| 3 | without | pale blue | blue-violet |
| | (1) | pale blue | blue-violet |
| | (2) | pale blue | blue-violet |
| | (3) | pale blue | blue-violet |
| | (4) | pale blue | blue-violet |
| | (5) | pale blue | blue-violet |
| | (6) | colourless | red |
| | (7) | pale blue | blue-violet |
| 1 + 3 | without | very pale blue | blue-violet |
| 2 + 3 | without | very pale blue | blue-violet |

Of course, the aforementioned embodiment has been described by way of example only and could be modified, inter alia by substitution of technical equivalents, without thereby departing from the scope of the invention.

We claim:

1. Thermochromic spiro heterocyclic compounds, selected from the group consisting of the following formulae;

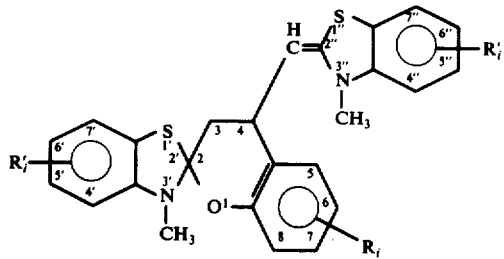

(1)

and

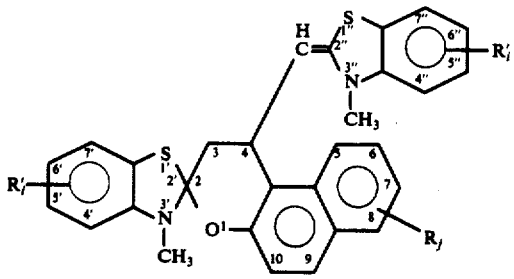

(2)

where $R_i$ is a substituent in positions 5, 6, 7 and 8 in formula (1); $R_i'$ is a substituent in positions 4', 5', 6' and 7' and 4", 5", 6" and 7" in formulae (1) and (2); and $R_j$ is a substituent in positions 5, 6, 7, 8, 9 and 10 in formula (2); wherein $R_i$ and $R_j$ are selected from the group consisting of hydrogen, alkyl, OH, OR, $NH_2$, $NR_1R_2$ and NHCOR, where R, $R_1$ and $R_2$ each denotes an alkyl radical; and wherein $R_i'$ is selected from the group consisting of hydrogen, alkyl, OH, OR, $NH_2$, $NR_1R_2$, NHCOR, $NO_2$, C≡N, $HSO_3$, CHO, COR, COOH, COOR, and halogen, where R, $R_1$ and $R_2$ each denotes an alkyl radical.

2. A compound according to claim 1 of the formula (1), where $R_i'$ and $R_i$ denote hydrogen atoms.

3. A compound according to claim 1 of the formula (1) where $R_i'$ denotes a hydrogen atom, $R_i$ denotes —$OCH_3$ in position 8 and hydrogen atoms in positions 5, 6 and 7.

4. A compound according to claim 1 of the formula (2) where $R_i'$ and $R_i$ denote hydrogen atoms.

5. A method of preparing a compound of claim 1 comprising condensing a quaternary benzothiazolium salt having the formula

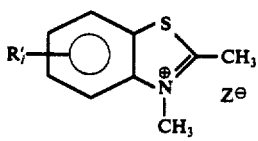

where $R_i'$ is as previously defined and Z is an anion, in the presence of a base and in a suitable solvent, with an aldehyde selected from the group consisting of a 2-hydroxy-benzaldehyde or ortho-hydroxy-naphthaldehyde, which may or may not bear the substituent groups $R_i$ and $R_j$, respectively, and wherein about two moles of quaternary salt are reacted for each mole of aldehyde, and recovering the product.

6. A thermographic recording element comprising a support having thereon a layer of a thermochromic composition containing at least one thermochromic compound selected from the group consisting of those having the formula:

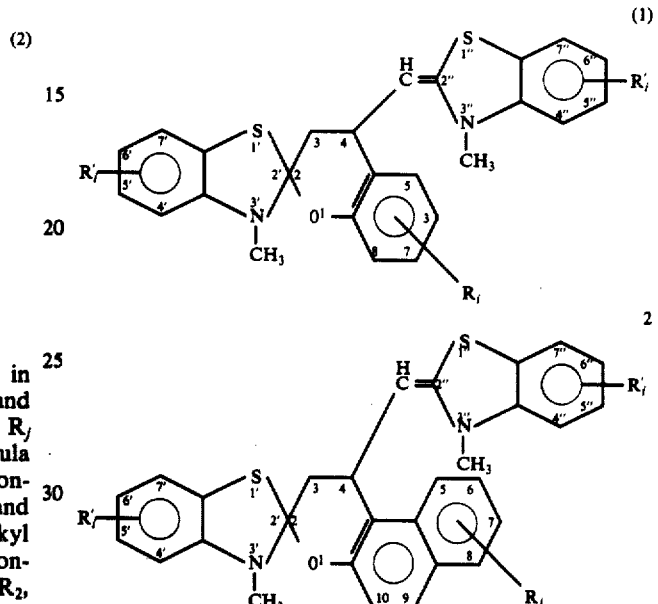

where $R_i$ is a substituent in positions 5, 6, 7 and 8 in formula (1); $R_i'$ is a substituent in positions 4', 5', 6' and 7' and 4", 5", 6" and 7" in formulae (1) and (2); and $R_j$ is a substituent in positions 5, 6, 7, 8, 9 and 10 in formula (2); wherein $R_i$ and $R_j$ are selected from the group consisting of hydrogen, alkyl, OH, OR, $NH_2$, $NR_1R_2$ and NHCOR, where R, $R_1$ and $R_2$ each denotes an alkyl radical; and wherein $R_i'$ is selected from the group consisting of hydrogen, alkyl, OH, OR, $NH_2$, $NR_1R_2$, NHCOR, $NO_2$, C≡N, $HSO_3$, CHO, COR, COOH, COOR, and halogen, where R, $R_1$ and $R_2$ each denotes an alkyl radical.

7. A thermographic recording element according to claim 6 wherein the composition further contains a reagent reactive with said compound to generate a color when whichever of the reagent and the compound which has the lower melting point is heated above its melting point, said reagent being selected from the group consisting of bis-2,2-(para-hydroxyphenyl)-propane, zinc stearate, cobalt stearate, manganese stearate, copper stearate, zinc chloride and manganese chloride.

* * * * *